United States Patent [19]

Schmidt

[11] Patent Number: 4,783,568
[45] Date of Patent: * Nov. 8, 1988

[54] XYLENE PRODUCING PROCESS HAVING STAGED CATALYTIC CONVERSION OF ETHYLBENZENE

[75] Inventor: Robert J. Schmidt, Rolling Meadows, Ill.

[73] Assignee: UOP Inc., Des Plaines, Ill.

[*] Notice: The portion of the term of this patent subsequent to Sep. 29, 2004 has been disclaimed.

[21] Appl. No.: 101,220

[22] Filed: Sep. 25, 1987

Related U.S. Application Data

[63] Continuation-in-part of Ser. No. 12,401, Feb. 9, 1987, Pat. No. 4,697,039, which is a continuation-in-part of Ser. No. 775,982, Sep. 13, 1985, Pat. No. 4,642,406.

[51] Int. Cl.$^4$ ............................................. C07C 5/22
[52] U.S. Cl. ................................. 585/477; 585/475; 585/478; 585/481
[58] Field of Search ................ 585/477, 478, 481, 475

[56] References Cited

U.S. PATENT DOCUMENTS

| | | | |
|---|---|---|---|
| 3,211,798 | 10/1965 | Burk, Jr. et al. | 260/668 |
| 3,464,929 | 9/1969 | Mitsche | 252/442 |
| 3,525,775 | 8/1970 | Bolton et al. | 260/668 |
| 3,636,180 | 1/1972 | Broughton | 260/668 A |
| 3,637,881 | 1/1972 | Williams et al. | 260/668 A |
| 3,701,813 | 10/1972 | Stenmark | 260/668 A |
| 3,780,121 | 12/1973 | Suggitt et al. | 260/672 T |
| 3,996,305 | 12/1976 | Berger | 260/672 T |
| 4,041,091 | 8/1977 | Henry | 260/672 T |
| 4,083,886 | 4/1978 | Michalko | 260/672 T |
| 4,101,596 | 7/1978 | Mitchell et al. | 260/668 A |
| 4,211,886 | 7/1980 | Tabak et al. | 585/321 |
| 4,341,914 | 7/1982 | Berger | 585/474 |
| 4,469,909 | 9/1984 | Chester et al. | 585/481 |

Primary Examiner—Curtis R. Davis
Attorney, Agent, or Firm—Thomas K. McBride; John F. Spears, Jr.

[57] ABSTRACT

A process is disclosed for the production of a desired xylene isomer, preferably paraxylene, and high quality benzene. The desired isomer (11) is recovered from the feed (1) and recycle (3) streams in a xylene separation zone (2). The raffinate (5) from the separation zone is passed into a catalytic xylene isomerization zone (6). The isomerization zone effluent stream is passed into a high severity transalkylation zone (14) which contains a catalyst comprising both a ZSM-5 zeolite and mordenite. Ethylbenzene in the feed stream is subjected to staged conversion in the two catalytic reaction zones to both xylenes and benzene. The overall ethylbenzene conversion efficiency is improved.

17 Claims, 1 Drawing Sheet

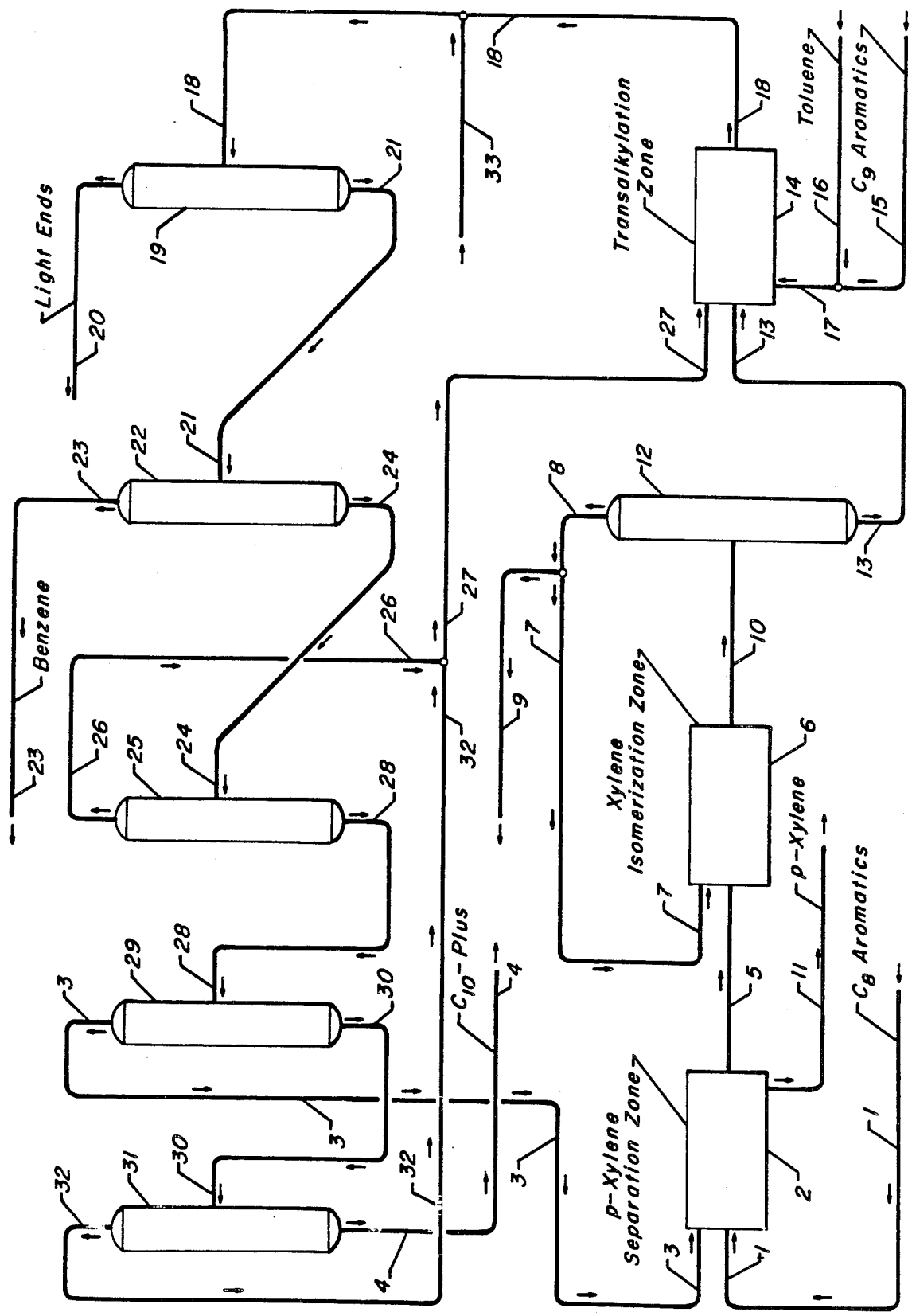

XYLENE PRODUCING PROCESS HAVING STAGED CATALYTIC CONVERSION OF ETHYLBENZENE

CROSS-REFERENCE TO RELATED APPLICATIONS

This application is a continuation-in-part of my prior application Ser. No. 12,401 filed Feb. 9, 1987 (now U.S. Pat. No. 4,697,039) which was a continuation-in-part of my prior application Ser. No. 775,982 filed on Sept. 13, 1985 (now U.S. Pat. No. 4,642,406) and which is incorporated herein by reference.

FIELD OF THE INVENTION

The invention relates to a hydrocarbon conversion process in which $C_8$ alkylaromatic hydrocarbons are produced. The invention also relates to an integrated process employing a catalytic reaction step in which a preferred xylene isomer is produced by a rearrangement reaction of other xylene isomers and a separation step in which the preferred xylene isomer is recovered by adsorptive separation from a mixture containing several xylene isomers. The invention also specifically relates to the transalkylation of $C_9$ and $C_7$ alkylaromatic hydrocarbons for the production of xylenes. The invention is specifically concerned with the overall process flow employed to produce additional amounts of the desired xylene isomer and high quality benzene from an ethylbenzene containing feed stream. The composition of specific catalysts or apparatus employed in the process is not a basic part of the subject matter of the invention.

INFORMATION DISCLOSURE

The production of specific xylene isomers is an important petrochemical process. For instance, large quantities of paraxylene are consumed as feed chemicals in the production of polyesters used in clothing manufacture. It is therefore important to be able to obtain high purity streams of one particular xylene isomer. This has led to the development of a number of xylene separation techniques. For instance, it is widely known that paraxylene may be separated from a mixture of two or more xylene isomers through partial crystallization. This separatory technique is employed in some commercial processes. A large amount of paraxylene is also recovered through the use of adsorptive separation techniques. Many available references describe suitable absorbents and operating techniques for the preferred method of recovering the desired xylene isomer as performed in the preferred embodiment of the subject process.

The ability to selectively recover one of the xylene isomers has further encouraged the development of xylene isomerization processes such as described in U.S. Pat. Nos. 3,464,929 issued to R. T. Mitsche and 4,101,596 issued to K. M. Mitchell et al. The latter reference is also pertinent for its showing that $C_8$ hydrocarbons recovered from the effluent of the isomerization zone by fractional distillation may be recycled to a paraxylene removal zone. This integration of the two steps of paraxylene isomerization and paraxylene separation are also shown in U.S. Pat. No. 3,636,180 issued to D. B. Broughton.

The higher commercial value of xylenes as compared to toluene and $C_9$ alkylaromatics has prompted the development of transalkylation processes, sometimes referred to as disproportionation processes, which produce xylenes from a feed stream of $C_7$ or $C_7$ and $C_9$ hydrocarbons. Transalkylation processes and catalysts are described in U.S. Pat. Nos. 3,996,305 issued to C. V. Berger and 4,083,886 issued to E. Michalko. The Berger reference illustrates the fractionation of the transalkylation zone effluent stream to produce a $C_8$ alkylbenzene product stream and a recycle stream of toluene and $C_9$ alkylbenzenes which are returned to the transalkylation zone.

A number of flow schemes which incorporate xylene isomerization, xylene separation, fractionation, and transalkylation into a single process have been developed. For instance, U.S. Pat. No. 3,211,798 issued to E. H. Burk Jr. et al. describes a process wherein both transalkylation and xylene isomerization are performed in a single moving bed reactor system. The same catalyst is therefore employed for both the transalkylation and isomerization reactions, with the feed points of the material to be isomerized and to be transalkylated and the operating conditions being chosen to promote the desired reactions. The use of synthetic gel catalysts and catalysts containing silica or silica and alumina are disclosed. This reference is believed not to teach the charging of an external toluene feed stream to the reaction zones. The reference suggests temperatures of from 800 to 975 degrees Fahrenheit (426 to 523 degrees Celsius) for transalkylation.

Other references which describe the use of isomerization, transalkylation and xylene recovery in a single process include U.S. Pat. Nos. 3,701,813 issued to D. G. Stenmark; 4,041,091 issued to M. J. Henry; and 4,341,914 issued to C. V. Berger. In the Berger reference, xylenes recovered from the feed stream and xylenes recovered by fractionation from the transalkylation zone effluent stream are both passed into a paraxylene separation-xylene isomerization loop.

U.S. Pat. No. 3,525,775 issued to A. P. Bolton et al. is pertinent for its teaching that disproportionation (migration of methyl groups from one ring to another ring) also occurs during the isomerization of xylenes. The reference also states in column 6 that a toluene-benzene fraction, a tri and higher methylbenzene fraction, and unrecovered xylene isomers can be recycled and combined with the feedstock. This is described as increasing the efficiency of utilization of the meta-xylene. The reference in column 4 et seq. describes the action caused in mildly "coking" the catalyst. This coking suppresses disproportionation of xylene, which appears to be considered as very beneficial to the overall process.

The Bolton reference also describes, in column 2, that the prior systems employing a noble-metal on alumina or silica-alumina supports in the presence of hydrogen should be operated above 800 degrees Fahrenheit (426 degrees Celsius) and preferably above 850 degrees F. (454 degrees Celsius) to limit the hydrogenation of the aromatic feed and products to naphthenic compounds.

U.S. Pat. No. 3,637,881 issued to A. H. Williams et al. describes a process for isomerizing alkylaromatic hydrocarbons with a catalyst comprising a Group VIII noble metal. The reference indicates that the transalkylation of $C_8$ aromatics will occur simultaneously with isomerization. U.S. Pat. No. 3,780,121 issued to R. M. Suggitt et al. describes a process for the disproportionation of alkylaromatics in the presence of a catalyst comprising hydrogen mordenite and a Group I-B metal. The process operates at mild temperatures (up to 399 degrees Celsius). The reference indicates that the isomerization of orthoxylene will occur simultaneously with orthoxylene disproportionation.

U.S. Pat. No. 4,211,886 issued to S. A. Tabek et al. is believed pertinent for its teaching as to the use of ZSM zeolite in catalysts for both xylene isomerization and for "heavy aromatics processing" in which benzene and xylene are produced from toluene and $C_9$-plus aromatics. The ZSM zeolite is however present in two different catalyst beds. One catalyst bed preferably contains a reduced acid activity catalyst to isomerize xylenes and selectively convert ethylbenzene and propylbenzene to benzene and ethane or propane respectively. The isomerization catalyst is described as preferably containing a Group VIII metal such as platinum or palladium. The heavy aromatics catalyst also preferably contains a metal hydrogenation function such as platinum or nickel.

U.S. Pat. No. 4,469,909 is also believed relevant for its teaching in regard to the ability of ZSM zeolites to catalyze various aromatic hydrocarbon transformations. For instance, it acknowledges the ability of a HZSM-5 with a metal to isomerize xylenes and to convert ethylbenzene by transalkylation to benzene and diethylbenzene. This reference is specific to the use of a platinum containing ZSM-5 material to convert $C_9$-plus material to benzene, toluene and xylenes plus light paraffins.

BRIEF SUMMARY OF THE INVENTION

The invention is a process for the production of benzene and a desired xylene isomer from a feed stream containing high concentrations of ethylbenzene in addition to one or more of the other xylene isomers. Conversion of ethylbenzene is staged, with some conversion occurring in each of two sequential reaction zones. A catalyst which is free of noble metals is employed at high severity operating conditions in a transalkylation zone in order to achieve the desired products. The invention is further characterized in that the transalkylation catalyst contains both a mordenite and a ZSM-5 zeolite. The process thereby provides a greater overall ethylbenzene conversion efficiency as described in more detail below.

The utility costs of the process are excellent because fewer fractionation columns are employed in the process and recycle rates are reduced. The subject process also produces a very high quality benzene product stream. A further advantage of the process is the high degree of flexibility provided by using two different types of reaction zones in series. These improvements are achieved by passing the raffinate stream of the xylene separation zone into a catalytic isomerization zone. Except for $C_6$–$C_7$ by-products and recycled naphthenes all of the net isomerization zone effluent is passed into a transalkylation zone, preferably in admixture with the $C_7$ and $C_9$ aromatic feeds normally charged to the transalkylation zone.

A broad embodiment of the subject invention may be characterized as a process for the production of a desired xylene isomer which comprises the steps of passing a first feed stream, which comprises ethylbenzene and at least two xylene isomers including the desired xylene isomer, and a hereinafter characterized first process stream, which comprises an admixture of xylene isomers, into a xylene separation zone, withdrawing a product stream comprising the desired xylene isomer from the xylene separation zone and also withdrawing a raffinate stream, which comprises ethylbenzene and an undesired xylene isomer, from the xylene separation zone; passing the raffinate stream into a catalytic xylene isomerization zone, wherein ethylbenzene is partially converted to xylenes, and producing a xylene isomerization zone effluent stream comprising all three xylene isomers; passing a second process stream, which comprises substantially all of the xylenes and ethylbenzene present in the isomerization zone effluent stream, and $C_9$ aromatic hydrocarbons, toluene, and a recycle stream comprising toluene into a catalytic transalkylation zone containing a nonmetal transalkylation catalyst comprising a ZSM zeolite and mordenite and operated at high severity conditions including a temperature over 426 degrees Celsius wherein ethylbenzene is partially converted primarily to benzene, and forming a transalkylation zone effluent stream which comprises benzene, toluene, $C_9$ aromatic hydrocarbons and all of the xylene isomers; separating the transalkylation zone effluent stream by fractional distillation and producing a benzene-rich process stream, which is withdrawn from the process as a product stream, a toluene-rich process stream, a xylene-rich process stream, and a third process stream, which comprises $C_9$ aromatic hydrocarbons; passing at least a portion of the toluene-rich process stream into the transalkylation zone as said recycle stream; and passing at least a portion of the third process stream into the xylene separation zone as said first process stream.

BRIEF DESCRIPTION OF THE DRAWING

The Drawing is a simplified flow diagram showing a preferred embodiment of the invention. $C_8$ aromatics including ethylbenzene entering the process through line 1 are separated in a separation zone 2 wherein paraxylene is recovered for removal through line 11. A paraxylene depleted raffinate stream comprising some orthoxylene and metaxylene is passed through line 5 into a xylene isomerization zone 6. All of the xylenes, ethylbenzene and heavier aromatics then flow through line 13 into the transalkylation zone 14. Each reaction zone affects both the conversion of ethylbenzene and also the isomerization of xylenes to establish an equilibrium concentration of the various xylene isomers.

DETAILED DESCRIPTION

Toluene and $C_9$ alkylaromatic hydrocarbons are presently produced at a much greater rate than is required to satisfy the demand for these hydrocarbons. There is however relatively strong and increasing demand for various xylenes, especially paraxylene. As already pointed out, xylenes are very valuable at feedstocks for many widely used petrochemicals and plastics. For instance, orthoxylene is used in the production of phthalic anhydride.

As set out above, various commercial processes have therefore been developed which convert less valuable toluene and $C_9$ alkylaromatics into xylene. These processes involve such molecular rearrangements as the transfer of the methyl groups of toluene to form benzene and xylenes or the transfer of the methyl groups of toluene and trimethylbenzenes to produce xylenes. Other $C_9$ aromatics may undergo other types of reactions. For example, ethyl groups may be transalkylated or dealkylated. These processes are sometimes referred to as disproportionation, but are referred to herein as transalkylation processes. Transalkylation thereby can be used to produce a mixture of xylene isomers. As also set out above, a desired xylene isomer can be separated out of a mixture of the isomers produced in a reaction zone, and the remaining isomers then passed through an isomerization zone to produce more of the desired xylene isomer.

The economic viability of any process for the production of xylenes is dependent on several factors. One of the most important of these is the total yield of the desired xylene isomer. An excessive production of undesired by-products or even valuable by-products such as benzene places a heavy economic burden on a process. Another important economic factor in the success of a commercial process is the initial capital cost of the equipment such as columns, reactors and piping and the catalyst necessary for operating the process. Finally, a successful process should have a low utilities cost. This is measured by the overall operating cost of the process which includes such utility items as heating and cooling streams associated with reactors and fractionation columns and the energy expended in compressing or pumping various fluid streams. It is an objective of the subject invention to provide a highly efficient process for the production of a desired xylene isomer. It is another objective of the subject invention to reduce the capital cost of a process for the production of paraxylene from a mixture of $C_8$ aromatics. It is a further objective of the invention to reduce the utilities cost of operating a process for the production of paraxylene from a mixture of $C_8$ alkylaromatic hydrocarbons which has a high concentration of ethylbenzene.

It has now been found that the xylene isomerization can be performed to essentially equilibrium conditions within a transalkylation zone employing a nonnoble metal transalkylation catalyst operated at high severity conditions. As described in my prior application, it is therefore unnecessary to provide a separate catalytic xylene isomerization reaction zone to reestablish xylene isomer equilibrium in the effluent stream of a xylene separation zone. This significantly lowers the complexity and cost of the process. An additional advantage is that the "ring loss" of aromatic compounds during passage through the transalkylation zone is much less than during passage through a xylene isomerization zone. The overall "ring" yield of a process employing only transalkylation is therefore normally greater than a process employing both isomerization and transalkylation zones.

In some instances, however, the optimum process arrangement is not determined solely by the yield of paraxylene. The total value of the benzene produced by dealkylation plus the value of paraxylene produced by isomerization must be balanced against the costs of an overall process. Processes providing reduced paraxylene yields due to higher benzene production have therefore begun to predominate due to their lower capital costs. However, when a high amount of ethylbenzene is present in the feed the conversion of the entire amount of ethylbenzene to benzene results in a relatively low xylene yield.

It is accordingly a further objective of the process to reduce the costs of processing feeds having high ethylbenzene concentrations while still providing good xylene yields. This objective is accomplished in the subject process by employing xylene isomerization and high severity toluene transalkylation processing zones in series with staged conversion of ethylbenzene in each zone.

A further objective, which is specific to this application, is to improve the yield of xylenes by increasing the selectivity of the catalyst employed in the transalkylation zone. It is also a specific objective of this application to provide an improved ability to convert ethylbenzene within the transalkylation zone.

In the subject process these specific objectives are achieved by employing within the transalkylation zone a catalyst comprising an admixture of a mordenite type zeolite and a ZSM zeolite. This catalyst is a metal-free catalyst and therefore does not contain such Group VIII metals as platinum, iron, nickel or palladium. Further details on preferred catalysts and alternative embodiments are given below.

An advantage of the subject process is improved conversion efficiency due to the higher overall conversion of ethylbenzene to benzene and additional xylenes. The overall $C_8$ aromatic hydrocarbon recycle rate and the size of the paraxylene recovery zone is reduced. Both initial capital expenditures and the utility costs of operating the process are accordingly lowered. The reduction in aromatics ring loss (lower loss per pass through the reactors) due to the presence of ZSM-5 in the transalkylation zone results in higher overall benzene and xylene isomer production yields. This set of improvements is referred to herein as improved conversion efficiency.

The feed stream or streams to the subject process may take several forms. The primary feed stream preferably contains an admixture of $C_8$ alkylaromatic hydrocarbons. Toluene and $C_9$ alkylaromatics such as trimethylbenzenes will normally also be charged to the process at one of a number of possible different points as secondary feed streams. These aromatic hydrocarbons can be obtained from a wide variety of sources such as by the liquefaction of coal, thermal cracking operations designed to produce olefinic hydrocarbons, and by extraction from crude oil fractions. The subject process is especially adapted to a $C_8$ feed stream derived from a pyrolysis naphtha as this material contains high amounts (e.g. 35–50 wt. %) of ethylbenzene. One widely used source of the feed aromatic hydrocarbons is a liquid-liquid extraction zone in which the aromatic hydrocarbons are selectively removed from a feed mixture having a selected boiling point range and containing a mixture of aromatic and nonaromatic hydrocarbons. A typical sequence for the production of the desired feed hydrocarbons therefore includes fractionation to produce a naphtha boiling range hydrocarbon mixture from a crude oil stream, the hydrotreatment of this fraction for the removal of sulfur, nitrogen, and other undesired compounds, the catalytic reforming of this fraction to increase the aromatic content, and a liquid-liquid extraction of the aromatics produced in this manner. The aromatics could also be separated from a wide boiling range reformate by extraction and fractionation. The feed(s) to the process may also be produced by fractionation without extraction.

As previously mentioned the subject process is especially suited to processing primary feed streams which contain a high concentration of ethylbenzene. This concentration is measured in terms of only the $C_8$ aromatic hydrocarbon portion of the primary feed stream. That is, the amount of $C_7$, $C_6$ or $C_9$ hydrocarbons in the primary feed stream is not considered in determining the $C_8$ concentration. As the primary feed stream is preferably a highly concentrated $C_8$ stream, the ethylbenzene concentration as measured in this manner will normally be close to the overall ethylbenzene concentration in this stream. The concentration of ethylbenzene in the feed stream is preferably greater than 25 wt. percent. It is highly preferred that the concentration of ethylbenzene in the $C_8$ portion of the feed stream is greater than 35 wt. percent.

The subject process may be operated with only a single $C_8$ containing feed stream plus required makeup streams of toluene and $C_9$ aromatic hydrocarbons required for transalkylation as depicted on the Drawing. Alternatively, the feed hydrocarbons may be charged to the process in different manners. For instance, the subject process could be operated with a feed stream containing $C_7$ through $C_9$ alkylaromatics being passed directly into the transalkylation zone or into one of the fractionation columns. The transalkylation effluent fractionation columns would then serve to also produce the feed to the xylene separation zone. It is also possible that the transalkylation zone may receive a toluene-rich feed stream containing xylenes and ethylbenzene.

It is apparent from the Drawing and this description that only minimal fractional distillation or other means of separation is required between the isomerization and transalkylation zones. Only light byproducts and hydrocarbons recycled to the isomerization zone reactor are removed from the isomerization zone effluent stream. It is to be noted that if naphthene production can be controlled or eliminated by means other than naphthene recycling, then even this minimal sparation may be deleted. This separation may also be deleted if it is desired or acceptable to produce significant amounts of naphthenes.

Those skilled in the art of hydrocarbon conversion process design will also recognize that it is possible for multicomponent feed streams to enter the process at a wide variety of different points depending on their composition. That is, the optimum point for a feed material to enter the process will be dependent upon its composition and the fractionation scheme which is employed in the process. The feed stream(s) may therefore be admixed with the transalkylation zone effluent stream, with the paraxylene separation zone raffinate stream or passed directly into any one of the fractionation columns illustrated in the Drawing. For instance, a toluene containing feed stream from an external source may be charged into the fractionation column which is preparing the toluene-containing recycle stream. At least 10 mole percent, and preferably at least 15 mole percent of the total hydrocarbons charged to the process as fresh feed is toluene. A toluene feed stream comprising mainly benzene and toluene would preferably be charged to the column producing the benzene product stream as a net overhead.

Heretofore integrated petrochemical complexes designed to convert a mixture of $C_7$ to $C_9$ alkylaromatic hydrocarbons to a single xylene would employ both a catalytic xylene isomerization zone and a catalytic transalkylation zone. The effluent from each zone would be fractionated in separate facilities to yield a xylene mixture then charged to the xylene separation zone. The subject process employs only a single series of fractional distillation columns to produce the product benzene, heavy by-product and recycle streams.

In the subject process transalkylation of toluene and $C_9$ alkylaromatics to xylenes, xylene isomerization and ethylbenzene dealkylation are performed simultaneously in the transalkylation reaction zone. This is one distinguishing feature of the subject process. The invention is also characterized by the charging of a considerable amount of both toluene and xylenes as fresh feed, the use of a noble metal-free transalkylation catalyst comprising both mordenite and a ZSM zeolite and the operation of the transalkylation reaction zone at high severity temperature conditions as described below. The charging of a large amount of ethylbenzene to the process and the staged conversion of ethylbenzene in the two reaction zones also characterize the subject process.

The operation of the subject process may be readily discerned by reference to the Drawing. In the drawing, a primary feed stream comprising an admixture of $C_8$ aromatic hydrocarbons containing all three xylene isomers and having a high concentration of ethylbenzene is passed through line 1 into the paraxylene separation zone 2. In the preferred embodiment of the invention the entering aromatics and any recycle $C_8$ aromatic hydrocarbons are contacted with a solid adsorbent which selectively retains paraxylene. This produces a paraxylene depleted stream which is referred to herein as the separation zone raffinate stream. This raffinate stream is discharged from the paraxylene separation zone through line 5. When the selective adsorbent becomes highly loaded with paraxylene, it is then contacted with a liquid phase desorbent which causes the paraxylene to be released from the adsorbent. A mixture of desorbent and paraxylene is withdrawn from the adsorption chamber. The paraxylene is then concentrated into the product stream by fractional distillation, which also recovers the desorbent. The desorbent is recirculated internally within the separation zone while the recovered paraxylene is discharged as a product stream withdrawn through line 11.

The paraxylene depleted raffinate stream is passed into a xylene isomerization zone 6. Within the xylene isomerization zone, the entering raffinate components and any recycled stream, such as the recycled naphthene of line 7, are contacted with a solid isomerization catalyst maintained at xylene isomerization promoting conditions as described herein. The catalyst and operating conditions are selected to perform a partial conversion of the ethylbenzene present in the raffinate stream to a mixture of xylenes. Simultaneously, the entering ortho and metaxylene present in the raffinate stream are in part isomerized to yield additional amounts of paraxylene. The effluent stream of the isomerization reactor is partially condensed to recover hydrogen for recirculation within the isomerization zone, and the liquid phase material recovered in this manner is passed through line 10 into a deheptanizer column 12. The deheptanizer column 12 is a single fractional distillation column designed and operated to separate the entering hydrocarbons into a net bottoms stream removed through line 13 and at least two overhead product streams. The overhead product is, for the sake of simplicity of presentation, shown as being withdrawn through line 8. That is, the overhead condenser, receiver and reflux system of this and the other columns is not shown on the Drawing. A process stream representing the relatively light hydrocarbons benzene and toluene is withdrawn from the process through line 9. This process stream will normally be withdrawn as a vapor phase stream removed from an overhead receiver of the column 12. The purpose of this stream is to balance the small rate of production of benzene and toluene within the somerization zone. The majority of the overhead material of deheptanizer column 12 comprises naphthenes. The production of these $C_8$ aromatic hydrocarbons within the xylene isomerization reactor can be limited to a large extent by recirculating naphthenes to the reaction zone. The recirculating naphthenes of line 7 therefore increases the overall xylene yield of the process.

The net deheptanizer column bottoms stream of line 13 will contain substantially all of the xylenes and ethylbenzene originally present in the isomerization zone effluent stream. This stream together with the recycle stream of line 27 is passed into a transalkylation zone 14. The recycle stream of line 27 will contain toluene and $C_9$ aromatic hydrocarbons. Additional amounts of toluene are charged to the process through the secondary feed stream of line 16, with $C_9$ aromatic hydrocarbons being charged through the secondary feed stream of line 15. The secondary feed streams enter the transalkylation zone through line 17.

Within the transalkylation zone, the admixture of entering hydrocarbons is contacted with a solid transalkylation catalyst maintained at high severity transalkylation conditions. These conditions and the catalyst are characterized herein. The conditions are chosen to complete the staged conversion of ethylbenzene, with ethylbenzene in this reaction zone being dealkylated to form benzene and ethane and ethylene. Toluene and $C_9$ aromatics entering the transalkylation zone are partially converted to a mixture of xylenes within the transalkylation zone. Entering ortho and metaxylene can also be converted to paraxylene at these conditions. In this manner there is produced a transalkylation zone effluent stream which will have a relatively low concentration of ethylbenzene, and will contain benzene, residual toluene, a near equilibrium concentration of the three xylene isomers, residual unconverted $C_9$ aromatics and the light ends produced as byproducts within the transalkylation zone.

The net transalkylation zone effluent stream is passed through line 18 into a stripping column 19. The stripping column 19, which could be located within and considered a part of the transalkylation zone 14, is designed and operated to separate the entering hydrocarbons into a $C_6$-plus net bottoms stream removed through line 21 and a net overhead stream comprising essentially all of the entering hydrocarbons which have five or fewer carbon atoms per molecule. The $C_6$-plus bottoms stream of column 19 is passed into a benzene column 22. The benzene column and the other columns are referred to in the traditional manner which refers to the primary component of the overhead stream of the column. Accordingly, a net overhead stream rich in benzene is withdrawn from column 22 via line 23. This high-purity benzene stream is discharged from the process as a net product stream. The benzene is a high value product suitable as a feed material to a large number of chemical and petrochemical processes.

The net bottoms stream of the benzene column is removed in line 24. This stream comprises the $C_7$-plus portion of the transalkylation zone effluent stream. It is separated within the toluene column 25 into the net overhead stream of line 26 and the net bottoms stream of line 28. The net overhead stream is a high-purity stream of toluene which preferably is recycled to the transalkylation zone via line 27. The bottoms stream of the toluene column contains the $C_8$-plus portion of the transalkylation zone effluent stream. This stream is separated in the xylene column 29 into the net overhead stream of line 3 and the net bottoms stream of line 30. The overhead stream of the xylene column should contain substantially all of the $C_8$ aromatic hydrocarbons present in the transalkylation zone effluent stream. The xylenes present in the transalkylation zone effluent stream are thereby transferred into the paraxylene separation zone 2 to allow the recovery of paraxylene. The net bottoms stream of line 30 should contain substantially all of the $C_9$ plus aromatic hydrocarbons present in the transalkylation zone effluent stream. This material is passed into a $C_9$ column 31 which separates substantially all of the $C_9$ aromatic hydrocarbons into the net overhead stream of line 32. All or a portion of the $C_{10}$-plus aromatic hydrocarbons are rejected as a net bottoms stream withdrawn from the process through line 4. The $C_9$ aromatics of line 32 are recycled to the transalkylation zone via line 27. As is known in the art, it is also in some instances desirable to recycle some of the $C_{10}$ or even heavier aromatic hydrocarbons to the transalkylation zone via the overhead stream of line 32 to increase the yield of xylenes by converting some of this heavier material to xylenes.

It is apparent from the Drawing and this description that only minimal fractional distillation or other means of separation is required between the isomerization and transalkylation zones. Only light by-products and hydrocarbons recycled to the isomerization zone reactor are removed from the isomerization zone effluent stream. It is to be noted that if naphthene production can be controlled or eliminated by means other than naphthene recycling then even this minimal separation may be deleted. This separation may also be deleted if it is desired or acceptable to produce significant amounts of naphthenes.

Those skilled in the art will recognize that as mentioned above there is considerable potential for variation in the feed location of one or more secondary feed streams to the process. To illustrate this fact an optional feed stream may be charged to the process through line 33. This feed stream could for instance be an admixture of $C_6$ to $C_{10}$-plus aromatic hydrocarbons. The various components of his optional feed stream would then be separated in the same manner as the transalkylation zone effluent stream in columns 19, 22, 25, 29 and 31. Another potential variation to the preferred embodiment shown in the Drawing comprises the further fractionation of the raffinate stream of the xylene separation zone to produce a stream rich in orthoxylene. In another possible variation to the subject flow, the xylene separation zone could be operated to produce a different xylene isomer as the product stream. That is, metaxylene could be removed from the separation zone as the product stream of line 11, with paraxylene being recycled through lines 5, etc. for the production of additional metaxylene.

As used herein, the term "substantially all" is intended to indicate an amount over 90 mole percent, and preferably over 95 mole percent, of the total amount of the compound or group of compounds referred to in the context of the term's usage. In a similar manner, the term "rich" is intended to indicate a molar concentration over 50 percent, preferably over 65 percent, of the indicated compound or class of compounds.

The term "staged conversion" is intended to indicate the total amount of conversion, as measured by disappearance from the specified initial feed stream, is divided between two different reaction zones such that at least one-third of the conversion occurs in each reaction zone. In the subject process, this means at least one-third (by weight % concentrations) of the ethylbenzene entering the isomerization zone must be converted to other compounds within the isomerization zone and that a second amount also equal to at least one-third of the ethylbenzene entering the isomerization zone must be converted within the transalkylation zone. Preferably, about 40 wt. % of the ethylbenzene is converted in each of the two conversion zones. In the isomerization zone at least 65, preferably 90, mole percent of the ethylbenzene converted within the isomerization zone is converted to xylenes. In the transalkylation zone at least 65, preferably 75, mole percent of ethylbenzene converted within this zone is dealkylated to benzene.

A preferred embodiment of the invention may accordingly be characterized as a process for the production of a desired xylene isomer which comprises the steps of passing a first feed stream, which comprises at least 25 wt. percent ethylbenzene based upon the $C_8$ content of the feed stream and also comprises at least two xylene isomers, and a hereinafter characterized recycle stream into a xylene separation zone, withdrawing a product stream comprising the desired xylene isomer from the xylene separation zone and also withdrawing a raffinate stream, which comprises ethylbenzene and an undesired xylene isomer, from the xylene separation zone; passing the raffinate stream into a catalytic xylene isomerization zone wherein the undesired xylene isomer is predominantly converted into the desired xylene isomer and ethylbenzene is partially converted to xylenes, and producing a xylene isomerization zone effluent stream comprising $C_8$ naphthenes and all three xylene isomers; separating $C_8$ naphthenes from the isomerization zone effluent stream by fractional distillation and recycling the thus separated $C_8$ naphthenes to the xylene isomerization zone, and thereby forming a first process stream comprising substantially all of the xylenes and ethylbenzene present in the isomerization zone effluent stream; passing the first process stream, toluene, $C_9$ aromatic hydrocarbons, and a second recycle stream into a catalytic transalkylation zone containing a nonmetal transalkylation catalyst comprising a ZSM-5 zeolite and mordenite and operated at high severity conditions including a temperature over 426 degrees Celsius and wherein ethylbenzene is predominantly converted to benzene and toluene is converted to xylenes, and producing a transalkylation zone effluent stream which comprises benzene, toluene, xylenes and $C_9$ aromatic hydrocarbons; separating the transalkylation zone effluent stream by fractional distillation and producing a benzene-rich process stream, which is withdrawn from the process as a product stream, a toluene-rich process stream, a xylene-rich process stream and a second process stream, which comprises $C_9$ aromatic hydrocarbons; passing at least a portion of the toluene-rich process stream into the transalkylation zone as said second process stream; and, passing at least a portion of the xylene-rich process stream into the xylene separation zone as said recycle stream.

The fractional distillation zone preferably is arranged as shown in the drawing and comprises five separate columns. However, as pointed out elsewhere the last column could possibly be deleted. For instance, if the presence of $C_9$-plus alkylaromatics is acceptable in the xylene separation zone feed then the stream of line 28 could be passed directly into the separation zone as the xylene-rich stream. In some instances another column would be used in the process. For instance, a feed stream to the overall process comprising $C_7$ through $C_9$ aromatics would preferably be separated in a prefractionation or splitting column not shown on the Drawing instead of entering via line 33. Such a combined feed could also be passed into column 25 and split therein into separate feed streams. Recovering pure streams of two different xylenes would also require the addition of another column.

It is believed that the equipment necessary to practice the subject invention such as fractionation columns, reactors, control systems, pumps, etc. may be designed, specified and built by those skilled in the art of petroleum/petrochemical process design and construction. Although rather complex, the equipment and adsorbent preferably used in performing the xylene separation step of the process may be of conventional nature similar to that now employed in the petrochemical industry.

The isomerization zone may be of any type or configuration which is capable of effecting the catalytic isomerization of orthoxylene and metaxylene into paraxylene at commercially acceptable rates and conditions. Moving bed reactors, fixed bed reactors and fluidized reactors may all be used to perform the isomerization reaction. These reactors are subject to further variation in that the hydrocarbon reactants may be passed through the catalyst as a vapor or as a liquid, and in that the reactor may be operated with upward, downward or radial reactant flow.

The isomerization zone is operated at conditions effective to cause the isomerization of ortho and metaxylene to paraxylene. In the presence of the catalysts described below these conditions include a temperature of about 200° C. to about 600° C., preferably 330° C. to about 420° C., and a pressure of from about 1.0 to 100 atmospheres. Preferred is a pressure in the range of about 7 to 28 atmospheres and the use of a single fixed-bed reactor operated with a downward flow of vapor phase reactants. The rate of hydrogen circulation should be sufficient to maintain a hydrogen to hydrocarbon mole ratio of from 1:1 to 20:1 in the reactor. This ratio is preferably kept within the range of about 1.5:1 to about 5:1. The amount of catalyst loaded in the reactor should provide a weight hourly space velocity (weight of hydrocarbons passing through the reactor in one hour per unit weight of catalyst) of about 0.5 to about 10 and preferably about 1 to 5. The exact conditions employed will normally vary with the age of the catalyst and are set by the activity of the catalyst and the effect of the conditions on selectivity, conversion and ultimate xylene yield of the isomerization zone.

Central to operation of the isomerization zone is an effective xylene isomerization catalyst. Several different suitable formulations are known to those skilled in the art and effective catalysts are available commercially. The catalyst will typically comprise an acidic inorganic oxide support such as alumina, silica-alumina mixtures, faujasites and mordenites which have been combined or impregnated with a metallic component. Preferred is an alumina based catalyst containing about 0.05 to about 5.0 wt. % of a Group VIII metallic component and 0.3 to 5.0 wt. % halogen. Particularly preferred is about 0.1 to about 1.5 wt. % of platinum or palladium and about 0.5 to 2.5 wt. % fluorine or about 0.1 to 1.5 wt. % chlorine. This halogen concentration may be maintained by the injection of halogen-containing substances such as carbontetrachloride into the material entering the isomerization zone. These catalytic composites may in addition contain from about 0.1 to about 1.0 wt. % sulfur to improve the performance. All percentages given in reference to catalyst composition are calculated on an elemental basis. Other catalysts which may be employed in the isomerization zone are described in some detail in U.S. Pat. Nos. 3,464,929; 3,409,685 and 3,409,686. The catalysts described in these references include an alumina matrix having less than 20 wt.% of finely divided mordenite dispersed in it and containing at least one metallic component chosen from nickel, platinum and palladium, about 0.001-2.0 wt. % sulfur and about 0.2 to 3.0 wt. % chlorine or fluorine. A second catalyst disclosed in these references has a base comprising an alumina matrix with less than 20 wt. % of finely divided mordenite dispersed in it and contains about 0.05 to 5.0 wt. % of platinum, or preferably palladium, and about 0.2 to 3.0 wt. % chlorine or fluorine. Other catalytic composites, including those not yet developed, may also be utilized.

The halogen content of the preferred catalysts set out above result in the liquid phase isomerate having a halogen content which it is desirable to remove prior to fractionation. This is typically performed by sequential washing with caustic, an alkaline aqueous solution, to remove the halogens and with water to remove carried-over caustic. This operation is performed in liquid phase conditions at temperatures of from about 20° to about 200° C. and a pressure which is between that of the isomerization zone and the deheptanizer. Washing operations are well known to those skilled in the art and may be deleted if not made desirable by the catalyst system used.

Another highly preferred isomerization catalyst comprises about 0.1 to 1.5 wt. percent of a platinum group metal, preferably platinum, supported on a base material containing a pentasil zeolite, preferably a ZSM zeolite, which have silica to alumina ratios above 20:1, and are defined in U.S. Pat. No. 3,702,886 (ZSM-5); 3,709,979 (ZSM-11) and 4,046,859 (ZSM-35). Preferably the zeolite will have a Constraint Index of from 1 to 12 and a dried crystal density of not less than 1.6 grams per cubic centimeter. The Constraint Index is described in an article entitled, "Catalysis by Crystalline Aluminosilicates: Characterization of Intermediate Pore-Size Zeolites by Constraint Index" in the *Journal of Catalysis*, Vol. 67, page 218 (1981) which is incorporated herein by reference.

A binder such as alumina, silica-alumina or silica will normally also be used in the support material to allow particle fabrication, provide strength and reduce catalyst costs. A highly preferred form of the isomerization catalyst is an extrudate containing between 10 and 70 wt. % ZSM-5 zeolite having the active metals uniformly dispersed throughout the catalyst. Preferably the catalyst will also contain about 0.1 to 2.5 wt. percent of a moderator metal such as tin, gallium, germanium, lead, indium or lithium. Specific details as to the composition and preparation of such isomerization catalysts are presented in U.S. Pat. No. 4,331,822, which is incorporated herein by reference.

The conditions employed in each of the fractionation columns may vary over a relatively wide range, with the required temperatures being controlled by the pressure at which each individual column is operated. The properties of the materials fractionated in this process are well known, and the design of suitable columns and the selection of proper operating conditions are well within the capabilities of those skilled in the art. Due to the increased cost of energy it is becoming a more common practice to operate the columns at a pressure of about 100 psig. or more and correspondingly high temperatures. This makes practical the use of heat removed in the overhead condenser of one column for reboiling a different column.

The feed stream to the process may contain a small amount of olefinic material. In addition, some olefins are normally produced in the isomerization zone. In order to remove these undesired impurities the bottoms stream from the deheptanizer 12 or stripping column 19 may be treated by passage as a liquid through a bed of suitable material. A proprietary clay such as Filtrol 24 supplied by the Filtrol Corporation is suitable for this purpose. This operation is carried out at a temperature of from 150° C. or lower to about 220° C. and a weight hourly space velocity of about 0.5 to 2.0. This clay is catalytically active and effects the oligomerization or polymerization of the olefins into relatively heavy hydrocarbons having more than eight carbon atoms and which are removed in the bottoms stream of the $C_9$ column 31. A clay treater is normally operated at a pressure of about 5 to 150 psig or as otherwise needed to maintain liquid phase conditions.

Typically, the admixture charged to the transalkylation reaction zone is first heated by indirect heat exchange against the effluent of the reaction zone and is then further heated in a fired heater. The resultant vaporous stream and hydrogen is then passed through the reaction zone, which may comprise one or more individual reactors. The use of a single reaction vessel having a fixed cylindrical bed of catalyst is preferred, but other reactor configurations utilizing moving beds of catalyst or radial flow reactors may be employed if desired. Passage of the feed admixture through the reaction zone effects the production of a vaporous effluent stream comprising hydrogen and both the feed and product hydrocarbons. This effluent is normally cooled by indirect heat exchange against the stream entering the reaction zone and then further cooled through the use of air or cooling water. The temperature of the effluent stream is normally lowered sufficiently to effect the condensation of substantially all of the feed and product hydrocarbons having six or more carbon atoms per molecule. The resultant mixed phase stream is passed into a vapor-liquid separator wherein the two phases are separated. The hydrogen-rich vapor is recycled. The condensate, which is referred to herein as the transalkylation zone effluent stream, is passed into the stripping column 19 in which substantially all $C_5$ and lighter hydrocarbons present in the effluent are concentrated into an overhead stream and removed from the process. This stripping column could be located within the transalkylation zone but is shown in the Drawing as column 19.

Sufficient hydrogen is admixed with the hydrocarbons which are passed into the transalkylation zone to form an admixture having a hydrogen to total hydrocarbon mole ratio above 2:1 and preferably above 5:1. The hydrogen to hydrocarbon mole ratio need not exceed 10:1 for successful operation of the process. This admixture is circulated through a bed of solid transalkylation catalyst located within a reaction zone as a vapor stream at an elevated temperature. The conversion which may be achieved within the reaction zone is limited by the thermodynamic equilibrium of the hydrocarbons which are present. For this reason, it is normally desired that the admixture contains only a small amount of any product hydrocarbon. Normally it would be preferred that the feed stream contains less than 2 mole percent of any product hydrocarbon. The production of xylenes in the isomerization zone makes this preference impossible in regard to the xylene concentration of the material entering the transalkylation zone. The preference for a low benzene concentration in the feed remains.

The conditions normally described for use in the transalkylation reaction zone include a temperature of from about 200 to about 525 degrees Celsius (about 392 to 977 degrees Fahrenheit). The subject process requires operation at high severity conditions as measured by reaction zone temperature and therefore cannot be performed successfully at the lower temperature portion of this broad range. The temperature required to maintain a desired degree of conversion will increase as the catalyst gradually loses activity during processing. Normal end-of-run temperatures may therefore exceed start-of-run (fresh catalyst) temperatures by 65 Celsius degrees or more. All reaction zone operating temperatures specified herein are start-of-run temperatures at the reactor inlet. It is essential that the reaction zone is operated at a temperature above 426 degrees Celsius (800 degrees Fahrenheit). It is preferred that the reaction zone start-of-run temperature is at least 438 degrees Celsius (820 degrees Fahrenheit) and more preferably at least 443 degrees Celsius (830 degrees Fahrenheit). Operations must normally be stopped at a temperature of about 487–498 degrees Celsius (910–930 degrees Fahrenheit) to prevent excessive thermal cracking and catalyst coking.

This high severity operating temperature is necessary to produce high quality benzene. Two factors combine to result in the production of more and better quality benzene at higher reaction conditions. The first factor is that the production of naphthenes is favored at lowered temperatures. This is basically because the naphthenes are not cracked as extensively at lower temperatures. The concentration of $C_7$ nonaromatics (paraffins and naphthenes) which are very difficult to separate from benzene by fractional distillation thereby increases in the transalkylation zone effluent stream as the temperature decreases. These compounds are the basic impurities in benzene. Since it is commercially impractical to remove them by fractionation their initial production must be limited to produce high quality benzene. The second factor which leads to the production of high quality benzene at high severity conditions is the increased rate of benzene production which occurs at higher temperature due to increased amounts of transalkylation. The larger amount of benzene results in more dilution of the nonaromatic impurities.

A large number of solid transalkylation catalysts have been developed. For instance, U.S. Pat. No. 3,729,521 describes 27 different catalysts which were tested for transalkylation activity and selectivity. The catalyst providing the best performance was prepared to contain 2.5 wt. % cobalt oxide and 10 wt. % molybdenum trioxide deposited on a support which contained 35 wt. % ultrastable, large-pore crystalline aluminosilicate material suspended in and distributed throughout a matrix of catalytically active alumina. In another embodiment, the ultrastable, large-pore crystalline aluminosilicate material is suspended in an amorphous silica-alumina cracking catalyst. Previously cited U.S. Pat. No. 3,849,340 describes a catalyst useful for the transalkylation of toluene which comprises a zeolite component having a mordenite crystal structure and having a silica to alumina mole ratio of at least 40:1 prepared by acid extracting alumina from an initial mordenite composition having a silica to alumina mole ratio of about 12:1 to 30:1 and a metal component selected from the group consisting of copper, silver, gold and zirconium.

The subject transalkylation reaction zone, however, preferably contains a catalyst similar to that described in U.S. Pat. No. 4,083,886, which is incorporated herein by reference, except that the catalyst will also contain a ZSM zeolite. The preferred mordenite is characterized by a method of preparation wherein a zeolite having a mordenite crystal structure and a sodium content of less than about 5 wt. % as $Na_2O$ is subjected to an aqueous ammoniacal treatment at a pH of at least about 9.5 and calcined in intimate admixture with a refractory inorganic oxide. The overall finished composite is a nonnoble metal catalyst, a term which is intended to indicate the catalyst does not contain ruthenium, rhodium, palladium, osmium, iridium or platinum or any combination of these metals at a concentration greater than 0.1 wt. % Preferably, the catalyst contains essentially none of these metals except for unintentional contaminants.

The catalyst must be free of any component which provides a "metal function" to provide a high quality benzene product. The catalyst should therefore be free of such elements as the Group IB or VIB metals such as copper, chromium, molybdenum or tungsten. The catalyst should also be free of the Group VIII metals such as iron, cobalt and nickel. The presence of even small amounts of the transition metals is considered undesirable as they tend to promote the hydrogenation of aromatics. The total concentration of all metals in the catalyst should be less than 0.10 wt. percent. A catalyst containing less than this amount of total metals is referred to herein as "nonmetal" or metal-free catalyst.

The catalytic component utilized in the transalkylation zone also comprises a ZSM zeolite in addition to the mordenite type zeolite. A ZSM-5 zeolite is preferred. A preferred range of zeolite contents is from 2 to 25 wt. % of a mordenite and from 5 to 25 wt. % of a ZSM-type zeolite. More preferably, the catalyst contains between 2 and 5 wt. % mordenite and the more preferred range for the ZSM component is from 10–15 wt. % of a ZSM-5 zeolite. The balance (50–88 wt. %) of the transalkylation catalyst is preferably alumina.

Like the isomerization catalyst, a separate binder may be present in the catalyst to provide strength and possibly to ease fabrication of catalyst particles. The alumina of the transalkylation catalyst may function as the binder. The finished transalkylation and isomerization catalysts may be in the form of cylindrical or shaped (polylobial, etc.) extrudates, pellets or spheres as formed by rolling or by an oil dropping technique. The oil dropping technique and subsequent processing are described in U.S. Pat. Nos. 2,774,743 and 2,787,599 which are incorporated herein by reference.

The paraxylene separation zone may use any one of several different separation techniques such as fractionation, crystallization or selective adsorption to remove paraxylene from the stream of mixed xylenes which enters the paraxylene separation zone. The preferred paraxylene separation zone contains a bed of molecular sieves operated in accordance with the teaching of U.S. Pat. No. 3,201,491 to simulate the use of a continuously moving bed of molecular sieves. Subsequent improvements to the process are described in U.S. Pat. Nos. 3,696,107 and 3,626,020. The preferred paraxylene separation zone is therefore operated at adsorption conditions which include temperatures in the range of from 30 to about 300 degrees Celsius, but preferably from 40 degrees to 250 degrees Celsius. This zone may be operated with either vapor phase or liquid phase process streams, with liquid phase operations being preferred. Pressures utilized may vary from atmospheric to about 1,000 psig, with more moderate pressures of from about 100 to 300 psig being preferred.

It is preferred that the molecular sieves are contained in one or more vertical columns, with the inlet and outlet positions of the feed stream, raffinate stream, extract stream and desorbent stream being periodically and unidirectionally shifted to simulate a continuous countercurrent moving bed of the adsorbent. The effluent streams of the adsorbent bed are fractionated as necessary to recover desorbent material which becomes admixed into both the raffinate and extract streams. The desorbent utilized in the process is recovered during this fractionation and recycled to the bed of adsorbent. This results in a continuous process which produces a xylene product stream containing over 98% paraxylene. A more detailed description of this process is contained in an article entitled, "The Parex Process for Recovering Paraxylene" which appeared at page 70 of *Chemical Engineering Progress,* Vol. 66, No. 9, Sept., 1970. Further details on the operation of the preferred paraxylene separation zone may also be obtained from U.S. Pat. Nos. 4,039,599 and 4,184,943 and the previously cited references which concern paraxylene separation. The paraxylene separation zone may depart from this preferred mole of operation through the use of batch-type operations or a true moving bed of solid adsorbent. The simulated cocurrent adsorptive separation process of U.S. Pat. No. 4,402,832 may also be employed. The extract and raffinate streams may be handled as described in these references or as described in U.S. Pat. No. 4,381,419.

The preferred adsorbent is a "molecular sieve" type adsorbent chosen from various natural and synthetic aluminosilicate adsorbents which exhibit an ability to preferentially adsorb selected xylene isomers. Preferred for use in the separation zone are synthetically prepared type X and type Y zeolites containing selected cations at the exchangeable cationic sites within the crystal structure. One suitable molecular sieve is a cation-exchanged type X or type Y zeolite containing a single cation selected from potassium, barium, sodium and silver. A second suitable molecular sieve is a type X or type Y zeolite containing both a first cation chosen from the group consisting of potassium, rubidium, cesium, barium and silver, and a second cation selected from the group consisting of lithium, sodium, magnesium, calcium, strontium, beryllium, cadmium, cobalt, nickel, copper, manganese and zinc. These molecular sieves are described in greater detail in U.S. Pat. No. 3,626,020. Other adsorbents, including those not yet developed, could be used if they meet the criteria of adequate selectivity and longevity necessary for commercial operation. Two other adsorbents which are suitable for paraxylene separation are described in U.S. Pat. Nos. 3,943,183 and 3,943,184.

What is claimed:

1. A process for the production of a desired xylene isomer which comprises the steps:
   (a) passing a first feed stream, which comprises ethylbenzene and at least two xylene isomers including the desired xylene isomer, and a hereinafter characterized first process stream, which comprises an admixture of xylene isomers, into a xylene separation zone, withdrawing a product stream comprising the desired xylene isomer from the xylene separation zone and also withdrawing a raffinate stream, which comprises ethylbenzene and an undesired xylene isomer, from the xylene separation zone;
   (b) passing the raffinate stream into a catalytic xylene isomerization zone, wherein ethylbenzene is partially converted to xylenes, and producing a xylene isomerization zone effluent stream comprising all three xylene isomers;
   (c) passing a second process stream, which stream comprises substantially all of the xylenes and ethylbenzene present in the isomerization zone effluent stream, and $C_9$ aromatic hydrocarbons, toluene, and a recycle stream comprising toluene into a catalytic transalkylation zone containing a nonmetal transalkylation catalyst comprising a ZSM-5 zeolite and mordenite and operated at high severity conditions including a temperature over 426 degrees Celsius wherein ethylbenzene is partially converted primarily to benzene, and forming a transalkylation zone effluent stream which comprises benzene, toluene, $C_9$ aromatic hydrocarbons and all of the xylene isomers;
   (d) separating the transalkylation zone effluent stream by fractional distillation and producing a benzene-rich process stream, which is withdrawn from the process as a product stream, a toluene-rich process stream, a xylene-rich process stream, and a third process stream, which comprises $C_9$ aromatic hydrocarbons;
   (e) passing at least a portion of the toluene-rich process stream into the transalkylation zone as said recycle stream; and,
   (f) passing at least a portion of the xylene-rich process stream into the xylene separation zone as said first process stream.

2. The process of claim 1 further characterized in that the desired xylene isomer is paraxylene.

3. The process of claim 2 further characterized in that the xylene separation zone is an adsorptive separation zone.

4. The process of claim 1 further characterized in that the transalkylation catalyst comprises about 2 to 25 wt. % of a zeolite having a mordenite structure and about 5 to 25 wt. % of a ZSM zeolite.

5. The process of claim 4 further characterized in that the concentration of ethylbenzene in the $C_8$ portion of the feed stream is greater than 25 wt. percent.

6. The process of claim 5 further characterized in that the transalkylation zone is operated at a temperature above 438 degrees Celsius.

7. The process of claim 6 further characterized in that the concentration of ethylbenzene in the portion of the feed stream is greater than 35 wt. percent.

8. The process of claim 4 further characterized in that the isomerization zone contains an isomerization catalyst comprising a ZSM-5 zeolite.

9. The process of claim 1 further characterized in that the separation zone comprises a crystallization separation zone.

10. A process for the production of a desired xylene isomer, which process comprises the steps:
   (a) passing a first feed stream, which stream comprises at least 25 wt. percent ethylbenzene based upon the $C_8$ content of the feed stream and also comprises at least two xylene isomers, and a hereinafter characterized recycle stream into a xylene separation zone, withdrawing a product stream comprising the desired xylene isomer from the xylene separation zone and also withdrawing a raffinate stream, which stream comprises ethylbenzene and an undesired xylene isomer, from the xylene separation zone;

(b) passing the raffinate stream into a catalytic xylene isomerization zone wherein the undesired xylene isomer is partially converted into the desired xylene isomer and ethylbenzene is partially converted to xylenes, and producing a xylene isomerization zone effluent stream comprising $C_8$ naphthenes and all three xylene isomers;

(c) separating $C_8$ naphthenes from the isomerization zone effluent stream by fractional distillation and recycling the thus separated $C_8$ naphthenes to the xylene isomerization zone, and thereby forming a first process stream comprising substantially all of the xylenes and ethylbenzene present in the isomerization zone effluent stream;

(d) passing the first process stream, toluene, $C_9$ aromatic hydrocarbons, and a second recycle stream into a catalytic transalkylation zone containing a nonmetal transalkylation catalyst comprising a ZSM-5 zeolite and mordenite and operated at high severity conditions including a temperature over 426 degrees Celsius and wherein ethylbenzene is converted primarily to benzene and toluene is converted to xylenes, and producing a transalkylation zone effluent stream which comprises benzene, toluene, xylenes and $C_9$ aromatic hydrocarbons;

(e) separating the transalkylation zone effluent stream by fractional distillation and producing a benzene-rich process stream, which is withdrawn from the process as a product stream, a toluene-rich process stream, a xylene-rich process stream and a second process stream, which comprises $C_9$ aromatic hydrocarbons;

(f) passing at least a portion of the toluene-rich process stream into the transalkylation zone as said second process stream; and, (g) passing at least a portion of the xylene-rich process stream into the xylene separation zone as said recycle stream.

11. The process of claim 10 further characterized in that the xylene separation zone is an adsorptive separation zone.

12. The process of claim 11 further characterized in that the transalkylation zone is operated at a temperature greater than 438 degrees Celsius and with a hydrogen to hydrocarbon mole ratio above 2:1.

13. The process of claim 10 further characterized in that the transalkylation catalyst comprises about 2 to 25 wt. % of a zeolite having a mordenite structure and about 5 to 25 wt. % of a ZSM-5 zeolite.

14. The process of claim 13 further characterized in that the transalkylation catalyst comprises between 2 to 5 wt. % of a mordenite type zeolite and between 10 to 15 wt. % of a ZSM-5 zeolite.

15. The process of claim 10 further characterized in that the isomerization catalyst comprises a ZSM-5 zeolite.

16. The process of claim 10 further characterized in that the desired xylene isomer is paraxylene.

17. The process of claim 16 further characterized in that the concentration of ethylbenzene in the $C_8$ portion of the feed stream is greater than 35 wt. percent.

* * * * *